US00RE38814E

(19) United States
(12) Reissued Patent
Wright

(10) Patent Number: US RE38,814 E
(45) Date of Reissued Patent: Oct. 4, 2005

(54) LOCAL CARDIAC IMMOBILIZATION SURGICAL DEVICE

(75) Inventor: John T. M. Wright, Denver, CO (US)

(73) Assignee: Genesee Biomedical, Inc., Denver, CO (US)

(21) Appl. No.: 09/226,764

(22) Filed: Jan. 6, 1999

Related U.S. Patent Documents

Reissue of:
(64) Patent No.: 5,782,746
Issued: Jul. 21, 1998
Appl. No.: 08/601,803
Filed: Feb. 15, 1996

(51) Int. Cl.[7] ..... A61F 2/00
(52) U.S. Cl. ..... 600/37; 128/897
(58) Field of Search ..... 600/37; 128/897–99; 623/1–3, 66

(56) References Cited

U.S. PATENT DOCUMENTS 4,973,300 A * 11/1990 Wright ..... 600/37
5,509,890 A * 4/1996 Kazama ..... 600/37
5,836,311 A * 11/1998 Borst et al. ..... 128/897

FOREIGN PATENT DOCUMENTS

WO WO 97/10753 3/1997

* cited by examiner

*Primary Examiner*—John P. Lacyk
(74) *Attorney, Agent, or Firm*—Swanson & Bratschun LLC

(57) ABSTRACT

A device and method for temporarily immobilizing a small segment of the surface of the heart during coronary artery bypass grafting for obviating the necessity for placing the patient on cardiopulmonary bypass are disclosed.

38 Claims, 3 Drawing Sheets

LOCAL CARDIAC IMMOBILIZATION SURGICAL DEVICE

Matter enclosed in heavy brackets [ ] appears in the original patent but forms no part of this reissue specification; matter printed in italics indicates the additions made by reissue.

FIELD OF THE INVENTION

This is a surgical device. The invention relates to surgery and, more specifically, to devices to assist in cardiovascular surgery the most common application of which will be performing coronary bypass surgery.

BACKGROUND OF THE INVENTION

Coronary bypass surgery is a frequently performed cardiac surgery. Approximately 320,000 patients undergo this procedure each year in the U.S. alone. Coronary artery bypass surgery is a technically delicate procedure, and surgeons routinely sew saphenous vein grafts or internal mammary arteries onto coronary arteries as small as one millimeter in diameter. Microsurgical instruments, optical magnification, very fine sutures and fine needles are all necessary to obtain the required precision. In a large majority of procedures the patient is placed on cardiopulmonary bypass as part of the operative procedure. Following commencement of cardiopulmonary bypass, the heart is arrested by the infusion of a cold cardioplegia solution into the coronary arteries and veins. By these means the surgeon is able to operate on a flaccid and motionless heart. Some surgeons have attempted to carry out bypass grafting on the beating heart, but the accuracy and delicacy of correct suture placement coupled with the increased operative time is such that it is difficult to routinely use this technique.

In most patients there is no medical reason to place patients on cardiopulmonary bypass, except to render the heart immobile so that the bypass graft can more easily be sewn onto the effected coronary artery.

Cardiopulmonary bypass is an expensive and complicated procedure in terms of drug therapy, personnel, equipment and prolonged operation time. It produces metabolic, hematologic and other disturbances to the patient, as well as requiring that the patient receive anticoagulation therapy during the bypass procedure, and reversal of anticoagulant following the cessation of cardiopulmonary bypass. Because of the residual volume of the cardiopulmonary bypass circuit, and the because the patient is anticoagulated, many patients have to receive blood transfusions during or following open heart surgery. Thus, the use of cardiopulmonary bypass has many drawbacks.

The present invention addresses the problems faced in coronary bypass surgery that arise from the need for cardiopulmonary bypass.

SUMMARY OF THE INVENTION

The device which is the subject of this invention addresses the issues related to coronary surgery and cardiopulmonary bypass procedures. The present invention is a method and apparatus for rendering temporarily and relatively immobile that area of the heart to which the coronary artery graft is to be attached during the anastomotic procedure. The use of the method and device allows the heart to beat in a relatively normal manner, and to pump enough blood to meet the metabolic meets of the patient, thus obviating the necessity to place the patient on cardiopulmonary bypass.

In one preferred form, the apparatus for immobilizing a surface portion of cardiac immobilizing member defines an elongate surface configured and constructed to lie in intimate contact with the surface of the heart of the patient and a layer of physiologically compatible adhesive for bonding the elongate surface temporarily to the surface tissue of the heart. The member is so constructed and configured to at least partially surround that portion of the heart upon which the surgical procedure is to be performed. The cardiac immobilizing member may be generally U-shaped or may generally define an annulus. In one preferred form, the cardiac immobilizing member has a minor diameter and a major diameter and the minor diameter is about one inch and the major diameter is about one and one-half inches. Also, in one preferred form, the cardiac immobilizing member at least partially comprises soft cushion seal of soft resilient conformable material, such as, for example, silicone rubber, synthetic rubber, natural rubber, or other resilient polymer, for partially conforming to the surface of the heart and being adhesively bonded to the heart surface.

The present invention is a device and method used to obtain local cardiac immobilization by temporarily attaching a rigid or semirigid cardiac immobilizing member to the heart by utilizing a partial vacuum between the boundaries of the cardiac immobilizing member and the surface of the heart. Leakage of fluid between the surface of the heart and the rigid cardiac immobilizing member is minimized by soft elastomeric seals placed in the leakage paths. The cardiac immobilizing member is placed on the outer surface of the heart so that the area of the heart to which the graft is to be sewn or otherwise attached lies approximately centered within the boundary formed by the inner seal. A controlled partial vacuum is then applied to the annular space bounded by the two seals, the body of the cardiac immobilizing member, and the surface of the heart. The cardiac immobilizing member, with the heart attached by force produced by the partial vacuum, is then raised slightly, and clamped to a substantially stationary body such as the sternal retractor which was used to open the chest by means of a suitable clamping means. This renders that area of the heart within the bound of the rigid annular cardiac immobilizing member relatively akinetic. If required, motion is also further minimized by the use of elastic retraction tapes place around the coronary artery adjacent to the anastomotic site.

Other methods may also be used to in association with the present invention to retain the cardiac immobilizing member stationary such as a hand held retractor or other retractor.

In one preferred embodiment of the device the cardiac immobilizing member is of elliptical form in plan view, and has a cross-section of appropriate shape as to provide sufficient rigidity to prevent flexibility. Soft elastomeric seals, preferably having a hardness value of in the general range of 5 to 50 on the Shore A scale formed of silicone rubber, or other soft resilient conformable material, are attached to the outer and inner periphery of the cardiac immobilizing member, such that an annular cavity is created between the seals, cardiac immobilizing member and the surface of the heart. One or more vacuum connecting tubes allow a partial vacuum to be drawn within the cavity. An attachment elongate rod fixed to the cardiac immobilizing member provides fixation means allowing the device to be rigidly attached to the sternal retractor, or to any other stationary fixture.

In another exemplary embodiment of the invention, the cardiac immobilizing member is used in a minimal surgical intervention method to restrain and immobilize an area of the heart which is exposed by means of a small incision in the thorax.

The present method is used as part of or in conjunction with a surgical method that comprises making an incision through the thoracic wall of a patient, and performing a surgical procedure proximate the surface of the heart. According to this invention, the method is improved by immobilizing a portion of the surface of the heart upon which surgery is to be performed. This is accomplished by placing an immobilizing member that defines at least one partial chamber in substantially fluid tight sealed relationship with the surface of the heart at least partially surrounding the portion of the surface of the heart upon which the surgery is to be performed to define at least one vacuum chamber and partially evacuating said vacuum chamber to secure the cardiac immobilizing device in sealed relationship to the heart and fixing the position of the cardiac immobilizing device. The surgical method can be carried out through an incision through the thoracic wall that is not substantially longer than the minor dimension of the cardiac immobilizing member.

The apparatus of the invention is for immobilizing a surface portion of the heart of a patient to enable a surgical procedure to be performed on the heart while the heart is beating. The apparatus comprises a cardiac immobilizing member comprising structure defining a partial chamber having edges, the edges being so constructed and configured to form a substantially fluid-tight seal with the surface of the heart, said member being so constructed and configured to at least partially surround that portion of the heart upon which the surgical procedure is to be performed and when in sealed relationship with the heart to define with the heart a vacuum chamber. Means are provided on or attachable to the cardiac immobilizing member for partially evacuating the vacuum chamber for securing said cardiac immobilizing member to the heart. Means are also provided for fixing the position of the cardiac immobilizing member. The cardiac immobilizing member, evacuating means and fixing means are so constructed and configured as to be attachable to the heart by reason of a partial vacuum in the partial chamber defined by the cardiac immobilizing member and substantially immobilizing that portion of the heart surface at least partially surrounded by the cardiac immobilizing member. The cardiac immobilizing member may generally define an annulus. The immobilizing member may be as small as to have a minor diameter is of from one-half to as large as one and one-half inches, optimally about one inch, and the major diameter of from about one inch to three inches, optimally about one and one-half inches. In a preferred embodiment, in the cardiac immobilizing member comprises walls at least partially formed of soft cushion seal silicone rubber, or other soft resilient conformable material, adapted to form a fluid tight seal with the surface membrane of the heart.

DESCRIPTION OF THE PREFERRED EMBODIMENTS

The invention is described by reference to exemplary, non-limiting embodiments.

Figure 2:
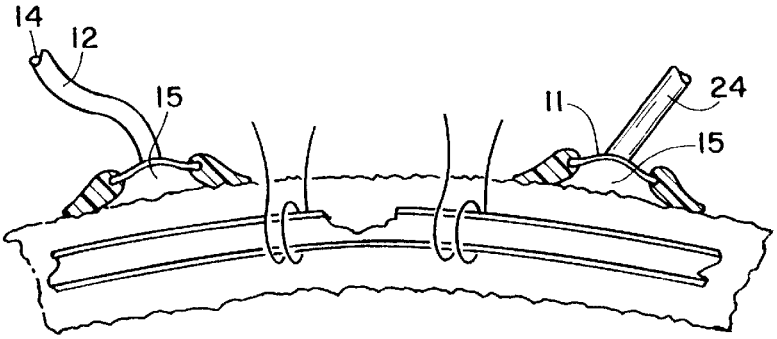
FIG. 2. shows a part cross-sectional view of the device in place on the heart.
Figure 3:
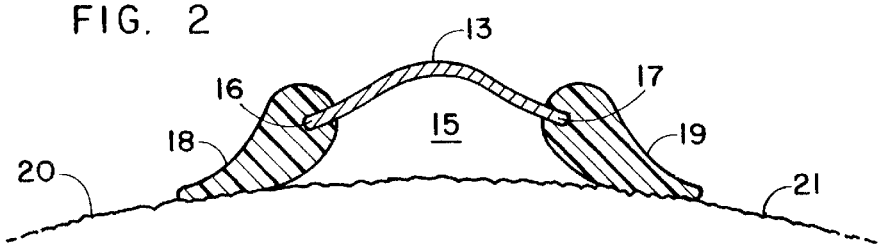
FIG. 3. shows a part cross-sectional view of the device taken along section 3—3 of FIG. 2.

Reference is now made to the drawings where like numbers refer to like elements in the drawings. The device to stabilize the beating heart during coronary bypass surgery 10, consists of a partially hollow U-shaped or circular or elliptical annulus 11. A generally elliptical annulus is preferred. This device functions as the cardiac immobilizing member. In cross-section, the cardiac immobilizing member is semicircular, arcuate or U-shaped, at least in part, defining one or more vacuum chambers. In the exemplary embodiment, one vacuum chamber 15, best shown in FIGS. 2 and 3 and one evacuation means 12, also best shown in FIGS. 2 and 3 is provided, but more than one may be defined by the cardiac immobilization member. The cardiac immobilization device comprises, referencing its normal position in use in the sense of up and down orientation, an upper face having depending walls extending downwardly toward the heart, the heart, the upper face and the walls defining a vacuum chamber. A tube 12, protrudes from the cardiac immobilizing member, preferably from the upper face 13 thereof. The inner bore 14 of the tube 12 communicates with the vacuum chamber 15. The depending walls, preferably, comprise the edges 16 and 17 (and the edge at the end of the "U" if the cardiac immobilizing device is U-shaped) of the upper face and soft cushion seals 18, 19. The lower edges of the seals, in use, lie adjacent to the outer wall of the heart in areas indicated at 20 and 21.

The cavity defined by the upper face 13, the walls 16 and 17, the seals 18 and 19, and the surfaces of the heart 20, 21 defines a space 15, which is a partial chamber, which, in use, contains a controlled partial vacuum drawn through connector 12 and flexible tube 23. This partial chamber, when sealed against the heart as described, and evacuated or partially evacuated is a vacuum chamber.

Figure 4:
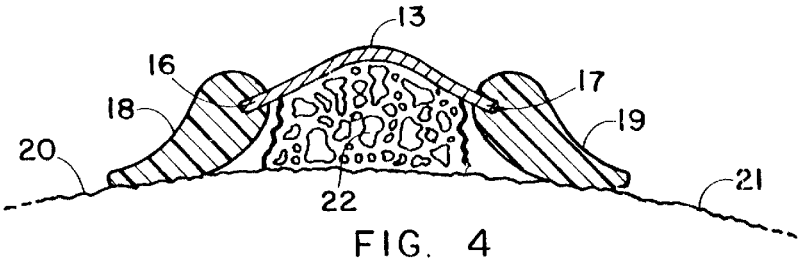
FIG. 4. shows a part cross-sectional view of an alternative embodiment of the device in a view corresponding to the view of FIG. 3.

In an alternative embodiment shown in FIG. 4 an open pore semi-rigid sponge, or other resiliently compressible material, 22 fills, or partially fills, the vacuum chamber to prevent the undue distortion of the myocardium, such as may occur if the chamber were excessively evacuated and the myocardium were pulled too far into cavity 15.

Figure 1:
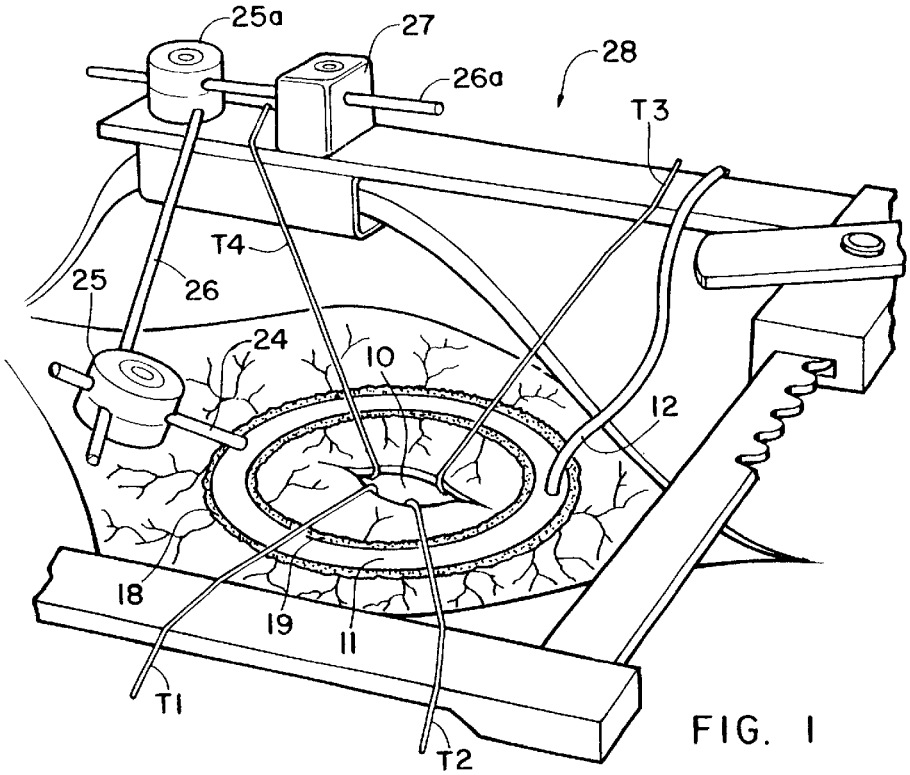
FIG. 1. shows an isometric view of the open chest with the heart exposed and the device attached to the heart, and an incision into the heart to expose the coronary artery.

Tube 12 may also be used as a mounting means. Alternatively, or in addition, as shown in FIG. 1 and FIG. 2, a separate mounting means 24 for the cardiac immobilizing member. The mounting means 24 is shown as an elongate rod, but virtually any substantially rigid mounting means may be used. This mounting means for cardiac immobilizing member may be clamped to the chest retractor 28 by means of suitable clamping means 25 and 25a and rods 26 and 26a and pillar clamp 27, of the retractor described in my copending patent application. Ser. No. 08/581,035, filed Dec. 29, 1995, is used. Any stationary object or fixture in the vicinity of the surgical field may, however, be used as the connection fixture for fixing the location of the cardiac immobilizing member and, hence, fixing the location of that surface region of the heart that is to be immobilized.

Figure 5:
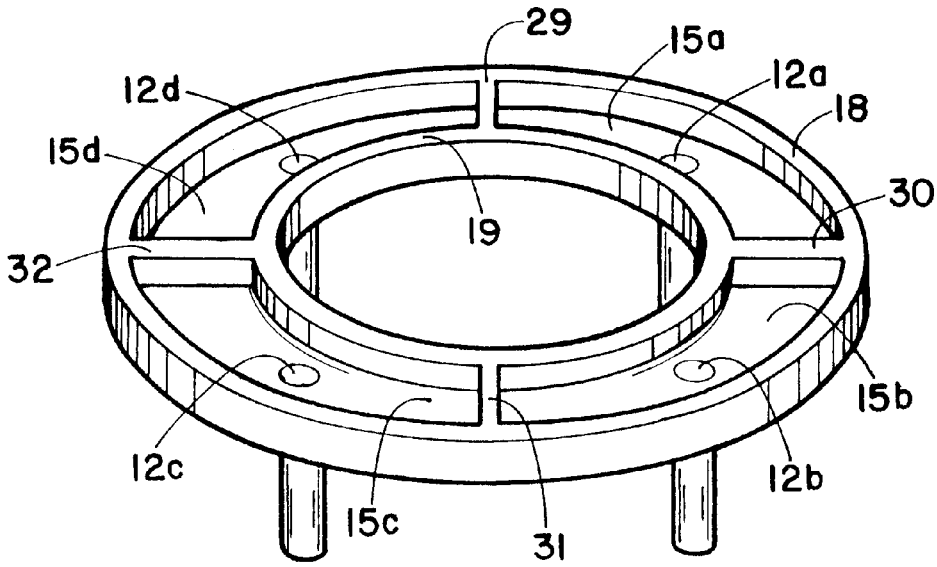
FIG. 5. shows an isometric under view of a second alternative embodiment the device.

In an alternative embodiment of the invention, shown in FIG. 5, the upper surface and walls that define, along with the heart, the vacuum chamber, is compartmentalized into two or more sections. In this arrangement, outer seal 18 and inner seal 19 are connected by ribs 29, 30, 31 and 32 which isolated cavities 15a, 15b, 15c and 15d from each other. Each cavity is partially evacuated via tubes 12a, 12b, 12c, 12d. Thus should leakge of air occur at a point on the inside or outside peripheral seal in one segment, the other three segments would not be affected and the area of the heart surface to which the cardiac immobilizing member is attached by the vacuum will remain essentially immobilized.

Figure 6:
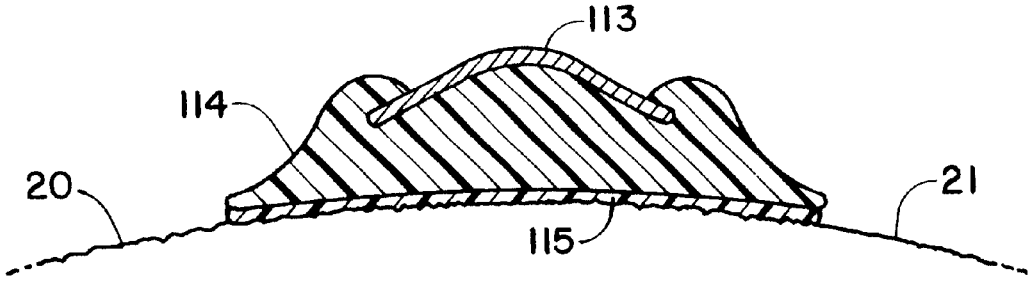
FIG. 6. shows a cross-sectional view of another alternative embodiment of the device in a view corresponding to the view of FIG. 3 wherein a physiological adhesive is used to secure the cardiac immobilizing member to the heart.

The alternative embodiment of FIG. 6 is simpler mechanically but requires the use of and removal of a physiologically compatible, preferably water soluble, adhesive to secure the cardiac immobilizing member to the heart. Referring now to FIG. 6 specifically, the configuration of the device may, as in the previous embodiments, be circular, elliptical or oval, U-shaped, or segmented, or in any other configuration that at least partially surrounds the area of the heart upon which surgery will be performed. In this embodiment, a generally rigid portion 113 is, preferably, attached to a surface-forming portion 114 of at least partially conformable physiologically compatible soft resilient conformable material, such as, for example, natural or synthetic rubber, silicone rubber, resilient or deformable polymer, which may be silicone rubber generally as previously described. A layer of physiologically compatible adhesive 115 underlays the surface of the cardiac immobilizing device and secures it to the surface of the heart. The member is so constructed and configured to at least partially surround that portion of the heart upon which the surgical procedure is to be performed. The cardiac immobilizing member may be generally U-shaped or may generally define an annulus. In a preferred form, the cardiac immobilizing member has a minor diameter and a major diameter and the minor diameter is about one inch and the major diameter is about one and one-half inches. Also, as suggested by the drawing, it is preferred that the cardiac immobilizing member at least partially comprises soft cushion resiliently deformable polymeric material for partially conforming to the surface of the heart and being adhesively bonded to the heart surface.

Figure 7:
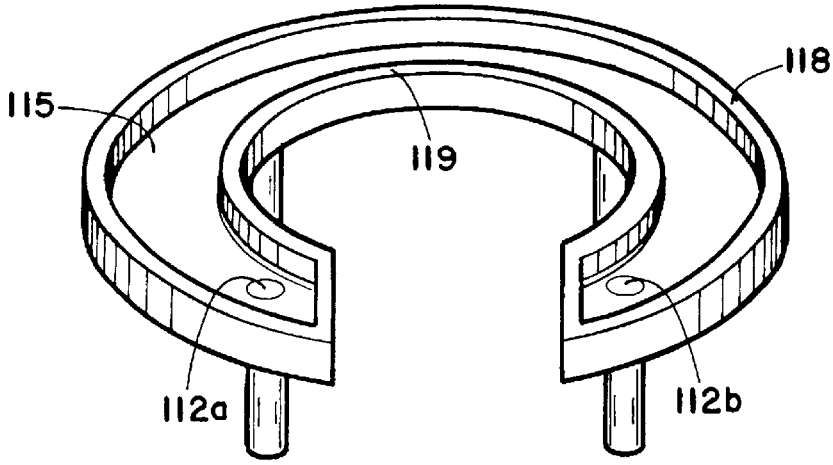
*FIG. 7 shows a top plan view of the U-shaped embodiment immobilizing device described in the specification.*

*The embodiment of FIG. 7 is similar to that shown in FIG. 5 except that the immobilization device is generally U-shaped with one vacuum chamber being shown for simplicity in illustration. The device comprises suction source inlet tubes 112a and 112b into the chamber 115 defined by walls 118 and 119.*

Various adhesive approaches may be used. The heart contacting surface of the cardiac, immobilizing member may be pre-coated with a physiologically compatible adhesive, or have such adhesive formed there on. The adhesive may be added as a separate component during the surgery or just before the surgical procedure beings. The adhesive must be sufficiently biocompatible as to dissipate harmlessly in body fluids or be removable with minimal difficulty. Water soluble biocompatible adhesives are known and are used in various surgical and medical procedures. Hydrogel polymers of hydroxyethylcellulose or hydroxymethylcellulose and hydrogel copolymers of these two, sometimes polymerized with acrylic acid and acrylic esters are well-known biocompatible adhesives. Such adhesives are fully and readily soluble in cold water. Polyvinyl alcohol is another water soluble adhesive that may be used. Any of the several physiologically acceptable, removable or water-soluble polymeric adhesives that are commercially available may be used.

Method of Use. When the device is to be used in an open chest operation the heart will usually exposed through a midline sternal incision and the chest retractor used to separate the sternum and the heart exposed. The stenosed coronary artery is identified and the device is place on the surface of the heart, so that it lies approximately centered about the operative site. A controlled partial vacuum is then applied to the device, which causes it to be clamped, limpet-like, to the surface of the heart. The clamping means is then connected to the sternal retractor, or other fixture, and the cardiac immobilization device, the heart is partially raised, and the clamping means tightened. Retraction tapes, $T_1$, $T_2$, $T_3$ and $T_4$, shown in FIG. 1., are then applied around the proximal and distal portions of the coronary artery. An incision is then made into the surface of the heart to expose the coronary artery. The ligatures are temporarily tightened, and an incision made into the coronary artery. If required a perfusion catheter is inserted into the distal coronary artery to perfuse the myocardium during graft anastomosis.

When the embodiment of FIG. 6 is used, the adhesive is placed on the device or the heart and the device secured to the heart by the adhesive, allowing sufficient time, if required, for the adhesive to dry or set up. The vacuum steps are, of course, eliminated. Otherwise, the procedure as described is followed. After the surgical procedure is complete, the adhesive is softened by swabbing or otherwise applying small amounts of water around the edges of the cardiac immobilizing member and the member is removed. Any remaining adhesive is removed by washing the area with water.

The device and method of this invention may, of course, be used in any surgical procedure performed on the exterior surface of the heart which does not interfere with the flow of blood into or from the heart chambers.

The device and method of this invention are particularly well adapted to minimally invasive surgical techniques wherein, for example, the actual surgical procedures are performed through a small incision using fluoroscopic or visual imaging and remote manipulations. These techniques have not been successful generally. One major impediment to these minimally invasive methods has been that it has been necessary, in order to still the heart, to place the patient on bypass which, in itself, is a severely traumatic procedure not easily adapted to being performed through small incisions. Using the present invention, the size of the incision need only be large, typically from about one to two inches long, enough to permit the cardiac immobilizing member to be positioned on the heart. Size and shape are not critical to the function of the device, but optimum results can often be achieved using cardiac immobilizing members from about ¾ to 1 inch wide and 1 to ½ long. The technique can be used, as part of any surgical procedure, to turn the heart without making a major incision to give access to a particular artery, vein or area of the heart. The method is the same as described above, except that the heart is turned and positioned before the cardiac immobilizing member is clamped in a fixed location.

Industrial Application

This invention is useful in veterinary and medical practice and in the health care equipment supply industry.

What is claimed is:

[1. In a surgical method comprising making an incision through the thoracic wall of a patient, and performing a surgical procedure proximate the surface of the heart, the improvement comprising immobilizing a portion of the surface of the heart upon which surgery is to be performed by temporarily securing to the surface of the heart a cardiac immobilizing member that at least partially surrounds the portion of the surface of the heart upon which the surgery is to be performed thereby substantially fixing the position of the cardiac immobilizing device, the step of securing the immobilizing member comprising applying a partial vacuum to the surface of the heart.]

[2. The method of claim 1 wherein the step of securing the cardiac immobilizing member to the heart further comprises applying a layer of physiologically compatible adhesive between the cardiac immobilizing member and the surface tissue of the heart.]

[3. In a surgical method comprising making an incision through the thoracic wall of a patient, and performing a surgical procedure proximate the surface of the heart, the improvement comprising immobilizing a portion of the surface of the heart upon which surgery is to be performed by placing a cardiac immobilizing member that defines at least one partial chamber in substantially fluid tight sealed relationship with the surface of the heart at least partially surrounding the portion of the surface of the heart upon which the surgery is to be performed to define at least one vacuum chamber and partially evacuating said vacuum chamber to secure the cardiac immobilizing device in sealed relationship to the heart and fixing the position of the cardiac immobilizing device.]

[4. The method of claim 3 the incision through the thoracic wall is substantially surrounded by the cardiac immobilizing member.]

[5. Apparatus constructed and adapted to immobilize a surface portion of the heart of a patient to enable a surgical procedure to be performed on the heart while the heart is beating comprising:

a cardiac immobilizing member comprising structure defining a partial chamber having edges, the edges being so constructed and configured to form a substantially fluid-tight seal with the surface of the heart, said member being so constructed and configured to at least partially surround that portion of the heart upon which the surgical procedure is to be performed and when in sealed relationship with the heart to define with the heart a vacuum chamber;

means for partially evacuating the vacuum chamber for securing said cardiac immobilizing member to the heart; and means for fixing the position of the cardiac immobilizing member;

said cardiac immobilizing member, evacuating means and fixing means being constructed, configured and adapted to be attachable to the heart by reason of a partial vacuum in the partial chamber defined by the cardiac immobilizing member and substantially immobilizing that portion of the heart surface at least partially surrounded by the cardiac immobilizing member.]

[6. The apparatus of claim 5 wherein the cardiac immobilizing member generally defines an annulus.]

[7. The apparatus of claim 6 wherein the cardiac immobilizing member has a minor diameter and a major diameter and the minor diameter is about one inch and the major diameter is about one and one-half inches.]

[8. The apparatus of claim 5 wherein the cardiac immobilizing member comprises walls at least partially formed of soft resiliently deformable polymeric material.]

[9. The apparatus of claim 5 wherein the cardiac immobilizing member defines a plurality of chambers.]

[10. The apparatus of claim 9 wherein the cardiac immobilizing member comprises walls at least partially formed of soft cushion seal resiliently deformable polymeric material.]

11. Apparatus constructed and adapted to immobilize a surface portion of the heart of a patient to enable a surgical procedure to be performed on the heart while the heart is beating comprising:

a cardiac immobilizing member comprising structure defining an elongate surface configured and constructed to lie in intimate contact with the surface of the heart of the patient and being so constructed and configured to at least partially surround that portion of the heart upon which the surgical procedure is to be performed;

a layer of physiologically compatible adhesive for bonding the elongate surface temporarily to the surface tissue of the heart; and means for fixing the position of the cardiac immobilizing member;

said cardiac immobilizing member and fixing means being constructed, configured and adapted to be attachable to the heart by the adhesive thereby substantially immobilizing that portion of the heart surface at least partially surrounded by the cardiac immobilizing member.

12. The apparatus of claim 11 wherein the cardiac immobilizing member generally defines an annulus.

13. The apparatus of claim 11 wherein the cardiac immobilizing member has a minor diameter and a major diameter and the minor diameter is about one inch and the major diameter is about one and one-half inches.

14. The apparatus of claim 11 wherein the cardiac immobilizing member at least partially comprises resiliently deformable [polymeric] material.

*15. In a surgical method comprising making an incision through the thoracic wall of a patient, and performing a surgical procedure proximate the surface of the heart, the improvement comprising:*

*immobilizing a portion of the surface of the heart upon which surgery is to be performed by:*

*temporarily securing to the surface of the heart a cardiac immobilizing member than at least partially surrounds the portion of the surface of the heart upon which the surgery is to be performed; and*

*substantially fixing the position of the cardiac immobilizing member;*

*the steps of securing the immobilizing member comprising applying a partial vacuum to the surface of the heart and applying a layer of physiologically compatible adhesive between the cardiac immobilizing member and the surface tissue of the heart.*

*16. In a surgical method comprising making an incision through the thoracic wall of a patient, and performing a surgical procedure proximate the surface of the heart, the improvement comprising:*

*immobilizing a portion of the surface of the heart upon which surgery is to be performed by:*

*placing a cardiac immobilizing member that defines at least one partial chamber comprising on a surface thereof a physiologically compatible adhesive in substantially fluid tight sealed relationship with the surface of the heart partially surrounding the portion of the surface of the heart upon which the surgery is to be performed, thereby forming a chamber comprising the partial chamber and the surface of the heart; and*

*creating a vacuum in said chamber to fix the position of the cardiac immobilizing member and at least partially immobilize the partially surrounded portion of the heart tissue.*

*17. In a surgical method comprising making an incision through the thoracic wall of a patient, and performing a*

*surgical procedure proximate the surface of the heart, the improvement comprising:*

*immobilizing a portion of the surface of the heart upon which surgery is to be performed by:*

*temporarily securing to the surface of the heart a U-shaped cardiac immobilizing member that at least partially surrounds the portion of the surface of the heart upon which the surgery is to be performed; and*

*substantially fixing the position of the cardiac immobilizing member;*

*the steps of securing the immobilizing member to the surface of the heart comprising applying a partial vacuum to the surface of the heart and applying a layer of physiologically compatible adhesive between the cardiac immobilizing member and the surface tissue of the heart.*

*18. In a surgical method comprising making an incision through the thoracic wall of a patient, and performing a surgical procedure proximate the surface of the heart, the improvement comprising:*

*immobilizing a portion of the surface of the heart upon which surgery is to be performed by:*

*placing a U-shaped cardiac immobilizing member that defines at least one partial chamber comprising on a surface thereof a physiologically compatible adhesive in substantially fluid tight sealed relationship with the surface of the heart partially surrounding the portion of the surface of the heart upon which the surgery is to be performed, thereby forming a chamber comprising the partial chamber and the surface of the heart; and*

*creating a vacuum in said chamber to fix the position of the cardiac immobilizing member and at least partially immobilize the partially surrounded portion of the heart issue.*

*19. In a surgical method comprising making an incision through the thoracic wall of a patient, and performing a surgical procedure proximate the surface of the heart, the improvement comprising:*

*immobilizing a portion of the surface of the heart upon which surgery is to be performed by:*

*temporarily securing to the surface of the heart an immobilizing member configured and constructed to define only one single chamber and to at least partially surround the portion of the surface of the heart upon which the surgery is to be performed; and substantially fixing the position of the cardiac immobilizing member;*

*the step of securing the immobilizing member comprising applying a partial vacuum through the cardiac immobilizing member to the surface of the heart.*

*20. In a surgical method comprising making an incision through the thoracic wall of a patient, and performing a surgical procedure proximate the surface of the heart, the improvement comprising:*

*immobilizing a portion of the surface of the heart upon which surgery is to be performed by:*

*placing a U-shaped cardiac immobilizing member that defines only one partial chamber in substantially fluid tight sealed relationship with the surface of the heart partially surrounding the portion of the surface of the heart upon which the surgery is to be performed, thereby forming a chamber comprising the partial chamber and the surface of the heart; and*

*creating a vacuum in said chamber to fix the position of the cardiac immobilizing member and at least partially immobilize the partially surrounded portion of the heart tissue.*

*21. Apparatus constructed and adapted to immobilize a surface portion of the heart of the patient to enable a surgical procedure to be performed on the heart while the heart is beating comprising:*

*a U-shaped cardiac immobilizing member defining only one U-shaped partial chamber configured and constructed to lie, when in use, in substantially fluid tight sealed relationship with the surface of the heart and to partially surround that portion of the heart upon which the surgical procedure is to be performed; and*

*means for producing a vacuum in said vacuum cup for fixing the position of the cardiac immobilizing member;*

*said cardiac immobilizing member being constructed, configured and adapted to be secured to the surface to the heart thereby substantially immobilizing that portion of the heart surface partially surrounded by the cardiac immobilizing member.*

*22. Apparatus constructed and adapted to immobilize a surface portion of the heart of the patient to enable a surgical procedure to be performed on the heart while the heart is beating comprising:*

*a generally U-shaped cardiac immobilizing cup defining a partial chamber and a layer of physiologically compatible adhesive on the cup, said layer being configured and adapted to lie, in use, against the surface tissue of the heart, said chamber being configured and constructed to lie, when in use, in substantially fluid tight sealed relationship with the surface of the heart and to partially surround that portion of the heart upon which the surgical procedure is to be performed; and*

*means for producing a vacuum in said vacuum cup for fixing the position of the cardiac immobilizing member;*

*said cardiac immobilizing member being constructed, configured and adapted to be secured to the surface to the heart thereby substantially immobilizing that portion of the heart surface partially surrounded by the cardiac immobilizing member.*

*23. In a surgical method comprising making an incision through the thoracic wall of a patient, and performing a surgical procedure proximate the surface of the heart, the improvement comprising:*

*immobilizing a portion of the surface of the heart upon which surgery is to be performed by:*

*temporarily securing to the surface of the heart a cardiac immobilizing member adjacent the portion of the surface of the heart upon which the surgery is to be performed and substantially fixing the position of the cardiac immobilizing member, said cardiac immobilizing member comprising structure that, in use, defines with the heart a closed chamber and enclosed in said chamber a member comprising open pore material;*

*the steps of temporarily securing said cardiac immobilizing member to the surface of the heart comprising applying a partial vacuum in said chamber to the surface of the heart with said open pore member in contact with the heart.*

*24. Apparatus constructed and adapted to immobilize a surface portion of the heart of the patient to enable a surgical procedure to be performed on the heart while the heart is beating comprising:*

*a cardiac immobilizing member comprising structure defining at least one partial chamber having edges, the edges being so constructed and configured to form a substantially fluid-tight seal with the surface of the heart and, enclosed in said chamber, a member comprising an open pore material, said cardiac immobilizing member being so constructed and configured to contact a portion of the heart adjacent that portion of the heart upon which the surgical procedure is to be performed and, when in sealed relationship with the heart, to define with the heart a partial vacuum chamber with said open pore material in contact with the surface of the heart;*

*means for partially evacuating the vacuum chamber for securing said cardiac immobilizing member to the heart; and*

*means for fixing the position of the cardiac immobilizing member;*

*said cardiac immobilizing member, evacuating means and fixing means being constructed, configured and adapted to be attachable to the heart by reason of a partial vacuum in the partial chamber defined by the cardiac immobilizing member and to substantially immobilize that portion of the heart surface adjacent the cardiac immobilizing member.*

*25. Apparatus for immobilizing a surface portion of the heart of a patient to enable a surgical procedure to be performed on the heart while the heart is beating comprising:*

*a cardiac immobilizing member comprising at least one partial chamber, each said partial chamber comprising walls terminating in edges, said walls at least partially formed of resiliently conformable material, each said partial chamber defining with the heart at least one vacuum chamber when said edges are in sealed relationship with the heart; and*

*means for communicating each partial chamber with a vacuum source.*

*26. The apparatus of claim 25 wherein said resiliently conformable material is selected from the group consisting of natural rubber, synthetic rubber, silicone rubber, resilient polymer and deformable polymer.*

*27. The apparatus of claim 25 further comprising a connector extending between a substantially stationary object and said cardiac immobilizing member.*

*28. The apparatus of claim 25 wherein said connector is substantially rigid.*

*29. The apparatus of claim 25 wherein said connector is an elongate rod.*

*30. The apparatus of claim 25 wherein said substantially stationary object is a sternal retractor.*

*31. The apparatus of claim 25 wherein said means for communicating each partial chamber with a vacuum source comprises a port.*

*32. The apparatus of claim 25 further comprising open pore material enclosed in each said partial chamber.*

*33. The apparatus of claim 32 wherein said open pore material at least partially fills each said partial chamber.*

*34. The apparatus of claim 25 wherein said cardiac immobilizing member is so configured to at least partially surround that portion of the heart upon which the surgical procedure is to be performed.*

*35. The apparatus of claim 34 wherein said cardiac immobilizing member surrounds on two opposing sides said portion of the heart upon which the surgical procedure is to be performed.*

*36. The apparatus of claim 34 wherein said cardiac immobilizing member surrounds on three sides said portion of the heart upon which the surgical procedure is to be performed.*

*37. The apparatus of claim 34 wherein said cardiac immobilizing member substantially surrounds said portion of the heart upon which the surgical procedure is to be performed.*

*38. The apparatus of claim 25 wherein said cardiac immobilizing member is U-shaped.*

*39. The apparatus of claim 25 wherein said cardiac immobilizing member is generally circular.*

*40. The apparatus of claim 39 wherein said cardiac immobilizing member is a closed circle.*

*41. The apparatus of claim 39 wherein said cardiac immobilizing member is an open circle.*

*42. The apparatus of claim 25 wherein said cardiac immobilizing member is generally elliptical.*

*43. The apparatus of claim 42 wherein said cardiac immobilizing member is a closed ellipse.*

*44. The apparatus of claim 42 wherein said cardiac immobilizing member is an open ellipse.*

*45. Apparatus for immobilizing a surface portion of the heart of a patient to enable a surgical procedure to be performed on the heart while the heart is beating comprising:*

*a cardiac immobilizing member comprising at least one partial chamber, each said partial chamber comprising a wall terminating in an edge, the edge being operably associated with a seal at least partially formed of resiliently conformable material, each said partial chamber defining with the heart a vacuum chamber when said seal is in sealed relationship with the heart; and*

*means for communicating each said partial chamber with a vacuum source.*

*46. Apparatus for immobilizing a surface portion of the heart of a patient to enable a surgical procedure to be performed on the heart while the heart is being comprising:*

*a cardiac immobilizing member comprising at least one partial chamber, each said partial chamber comprising an upper face and downwardly-extending walls terminating in edges, the edges being operably associated with a seal at least partially formed of resiliently conformable material, each said partial chamber defining with the heart at least one vacuum chamber when said seals are in sealed relationship with the heart, said cardiac immobilizing member being so configured to at least partially surround that portion of the heart upon which the surgical procedure is to be performed; and*

*means for communicating each partial chamber with a vacuum source.*

*47. Apparatus for immobilizing a surface portion of the heart of a patient to enable a surgical procedure to be performed on the heart while the heart is beating comprising:*

*a cardiac immobilizing member comprising at least one partial chamber, each said partial chamber comprising resiliently conformable edges, each said partial chamber defining with the heart at least one vacuum chamber when said edges are in sealed relationship with the heart; and means for communicating each partial chamber with a vacuum source.*

*48. In a surgical method comprising making an incision through the thoracic wall of a patient, and performing a surgical procedure proximate the surface of the heart, the improvement comprising:*

*immobilizing a portion of the surface of the heart upon which surgery is to be performed by temporarily securing to the surface of the heart by application of a partial vacuum a cardiac immobilizing member and substantially fixing the position of the cardiac immobilizing member;*

*said cardiac immobilizing member comprising portions formed of resiliently deformable material for forming a seal with the heart tissue.*

* * * * *